United States Patent [19]

Seyler et al.

[11] Patent Number: 5,409,001
[45] Date of Patent: Apr. 25, 1995

[54] MEDICAL THERAPY SYSTEM

[75] Inventors: Gerhard Seyler, Bubenreuth; Gerd Huettenrauch, Uttenreuth; Hans-Peter Seubert, Heroldsbach, all of Germany

[73] Assignee: Siemens Aktiengesellschaft, Munich, Germany

[21] Appl. No.: 823,090

[22] Filed: Jan. 15, 1992

Related U.S. Application Data

[63] Continuation of Ser. No. 524,041, May 16, 1990, abandoned.

[30] Foreign Application Priority Data

May 30, 1989 [EP] European Pat. Off. ......... 89109729

[51] Int. Cl.$^6$ ................................................. A61B 17/22
[52] U.S. Cl. ..................................... 128/653.1; 601/4
[58] Field of Search .................... 128/653.1, 660.03; 601/2–4; 606/130; 318/628, 638; 607/97

[56] References Cited

U.S. PATENT DOCUMENTS

| | | | |
|---|---|---|---|
| 3,995,205 | 11/1976 | Klees | 318/588 |
| 4,763,652 | 8/1988 | Brisson et al. | 128/24 EL |
| 4,787,394 | 11/1988 | Ogura | 128/24 EL |
| 4,821,729 | 4/1989 | Makofsi et al. | 128/24 EL |
| 4,829,986 | 5/1989 | Eichler et al. | 128/24 EL |
| 4,869,239 | 9/1989 | Krauss et al. | 128/24 EL |
| 4,955,366 | 9/1990 | Uchiyama et al. | 128/24 EL |

FOREIGN PATENT DOCUMENTS

| | | |
|---|---|---|
| 0269801 | 9/1987 | European Pat. Off. . |
| 0288698 | 3/1988 | European Pat. Off. . |
| 3736733 | 5/1988 | Germany . |
| 3122056 | 11/1988 | Germany . |

*Primary Examiner*—Ruth S. Smith
*Attorney, Agent, or Firm*—Hill, Steadman & Simpson

[57] ABSTRACT

A medical therapy system includes an x-ray system for locating a treatment site in a patient and a therapy device for administering medical therapy. Apparatus is provided for supporting and positioning the therapy device, which includes a computer into which the position of the therapy device can be entered with reference to the x-ray images, with automatic positioning of the therapy device being undertaken based on the entered data.

3 Claims, 1 Drawing Sheet

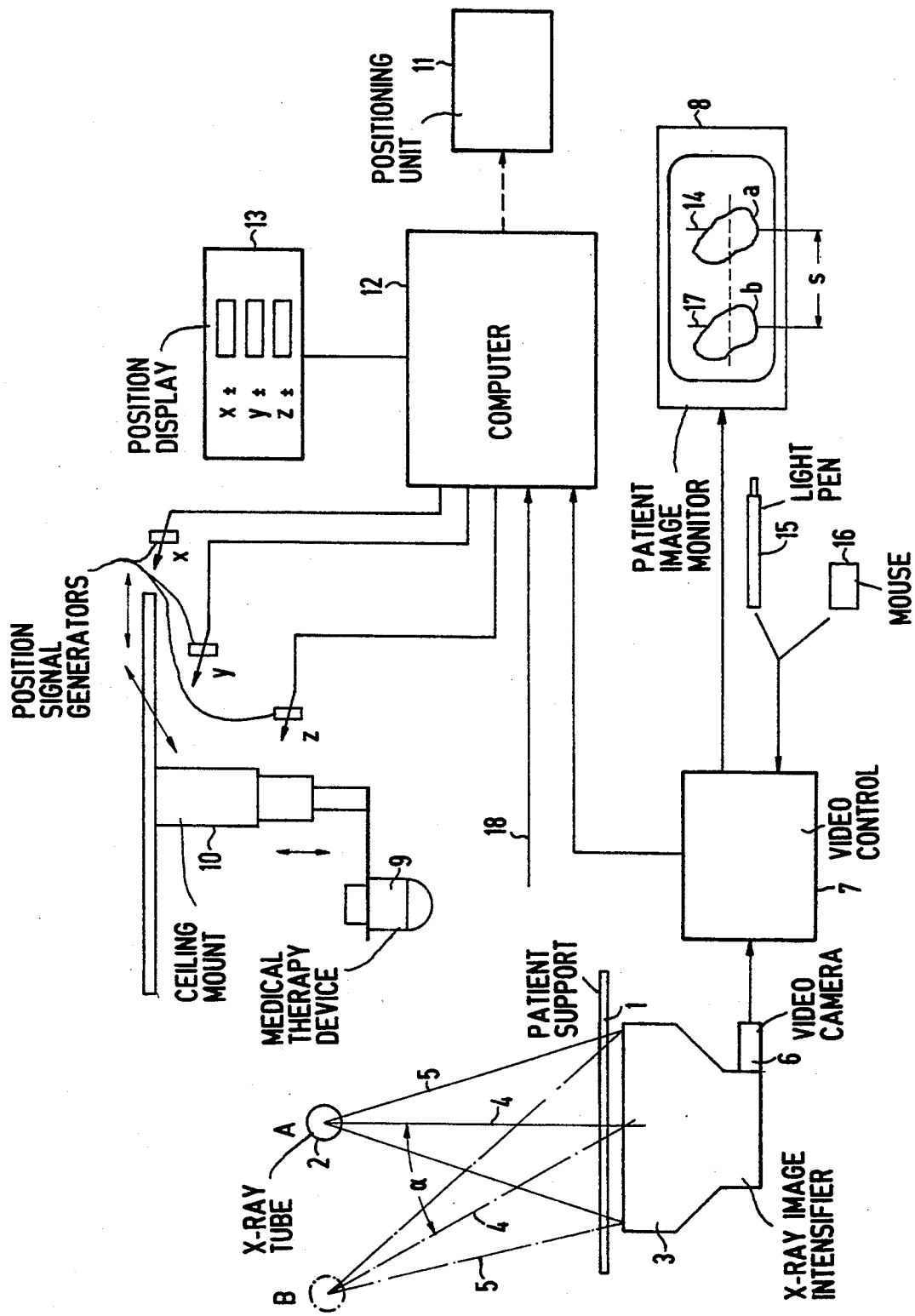

MEDICAL THERAPY SYSTEM

This is a continuation of application Ser. No. 524,041, filed May 16, 1990, now abandoned.

BACKGROUND OF THE INVENTION

1. Field of the Invention

The present invention is directed to a medical therapy system, and in particular to such a system which includes a medical therapy device and a locating system for acquiring information regarding the spatial position of selected regions of a patient to whom therapy is to be administered, and an apparatus for positioning the therapy device to administer the therapy. The positioning apparatus may be motor-driven or manually operable.

2. Description of Prior Art

Medical therapy devices, such as devices for generating shock waves to disintegrate a calculus in the body of a patient, are incorporated in a therapy system, which usually includes devices for obtaining an image of a treatment site of the patient, and supporting apparatus for the therapy device. If the therapy device is a shock wave generator, the shock waves will be emitted focused at a focal region. It is thus necessary to position the shock wave generator for administration of the treatment so that the focal region coincides with the in situ location of the calculus to be disintegrated.

SUMMARY OF THE INVENTION

It is an object of the present invention to provide a medical therapy system wherein a simple and exact positioning of the therapy device is achieved.

This object is achieved in accordance with the principles of the present invention in a medical therapy system wherein adjustment of the position of the therapy device is automatically controlled by a computer into which the therapy position of the therapy device (which is the position, relative to the treatment site in the patient, necessary to properly administer the desired medical therapy) is entered with respect to patient image information. Upon transirradiation of the patient with an x-ray unit from two different directions, data regarding the spatial position of an in situ calculus can be obtained. The data are entered into a computer which automatically re-adjusts the position of the therapy device so that, if the therapy device is a shock wave generator, the calculus is disposed in the focal region of the shock wave generator. Correct positioning of the therapy device is thus achieved in an economic manner, because an x-ray locating system for examination of the patient is already present, and a relatively low additional outlay is needed for the positioning components.

In a preferred embodiment of the invention, a monitor is provided for displaying the x-ray images, with a marking means for entering the therapy position of the therapy device needed to properly administer its desired medical therapy in the displayed image being provided. The therapy position can be entered on the monitor display using, for example, a light pen, a mouse, a tracking ball or the like.

DESCRIPTION OF THE DRAWINGS

The single FIGURE is a schematic block diagram of a medical therapy system constructed in accordance with the principles of the present invention.

DESCRIPTION OF THE PREFERRED EMBODIMENTS

As shown in the drawing, a medical therapy system constructed in accordance with the principles of the present invention includes a patient support 1 on which a patient to whom the medical treatment is to be administered lies. The patient is transirradiated by an x-ray locating system, including an x-ray tube 2 and an x-ray image intensifier 3. The x-ray tube 2 generates an x-ray beam 5, in which the patient is disposed, having a central ray 4. The x-ray tube 2 can be placed at two positions A and B, so that the central ray 4 describes an angle $\alpha$, the x-ray tube 2 can thus be said to pivot about a point at which the central rays 4 intersect when the x-ray tube is at positions A and B. The output image of the stationary x-ray image intensifier 3 is recorded by a video camera 6, and is reproduced on a patient image monitor 8 via a video control 7, having an image memory.

A medical therapy device 9, such as a shock wave generator, is suspended by a ceiling mount 10 so as to be three-dimensionally positionable. The three coordinates in which the medical therapy device 9 is adjustable are referenced x, y and z. Adjustment of the medical therapy device 9 along the coordinates x, y and z ensues with a positioning unit 11. The positioning unit 11 may, for example, include electric motors respectively allocated to the coordinates x, y and z, or may be a manual positioning unit, in which case positioning will ensue by loosening of the support brakes in the ceiling mount 10, and by zero balancing of a difference display 13.

A computer 12 compares the actual position of the medical therapy device 9 (x, y and z signals obtained from respective position signal indicators) to the therapy position needed to administer the desired there with reference to the monitor 8, and controls operation of the positioning unit 11 such that the actual position and the rated position coincide. The difference display 13 indicates the difference between the actual position and the prover therapy position.

Locating of a treatment site in the patient, such as the in situ position of a calculus to be disintegrated, and the positioning of the medical therapy device 9 take place in the following sequence. The x-ray tube 2 is located at position A so that the central ray 4 is vertical. This results in the treatment site, such as the calculus, being shown on the monitor 8 at position a, referenced to the reference mark 14.

The x-ray tube 2 is then pivoted by the angle $\alpha$.

The treatment site (calculus) migrates in the video image on the monitor 8 by a distance s which is proportional to its path on the input luminescent screen of the x-ray image intensifier 3. The treatment site is now located at position b on the monitor 8.

The location of the treatment site at position b is marked on the monitor by any one of a number of data entry devices, such as a light pen 15, a mouse 16, a tracking ball (not shown), or the like. This results in the mark 17 being shown on the monitor 8.

The difference between the position a, corresponding to the reference mark 14, and the position b, corresponding to the mark 17, i.e. the path s, is entered in the computer 12.

The height of the treatment site above the pivot point is calculated in the computer 12 from the path s, the position of the pivot point for the x-ray tube 2, the angle $\alpha$, and the distance of the focus image plane. The current device positions corresponding to the distance s, the position of the pivot point, the angle α and the distance of the focus image plane are entered at line 18. The position of the treatment site in space can now be defined.

The computer 12 now calculates the difference between the position of the treatment site and the position of the focal region of the medical therapy device 9, and displays this difference at the difference display 13 in the spatial coordinates x, y and z. If the positioning unit 11 is provided (which is not necessary if manual positioning is to be undertaken) the difference values are forwarded to the positioning device 11.

The ceiling mount 10 is adjusted so that, either manually or via the positioning unit 11, the actual position of the focal range of the medical therapy device 9 coincides with the therapy position prescribed by the spatial position of the treatment site. The focal range and the treatment site now lie at the same spatial location, and therapy can begin.

The above-described medical therapy system has a simple structure, wherein an exact positioning of the medical therapy device 9 is possible. The portion of the device consisting of the components 1 through 6, in combination with the video control 7 and the monitor 8, permits x-ray examinations with oblique transirradiation of the patient to be undertaken, apart from the use of those components in positioning of the medical therapy device 9.

The above system has been described using the example of a shock wave generator as the medical therapy device 9. The system, however, can be used to position any type of medical therapy device. It is also possible to use a locating system other than an x-ray system, such as an ultrasound locating system.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical therapy system comprising:

means for administering medical therapy to a patient at a treatment site;

x-ray locating means for generating data identifying the spatial position of said treatment site in said patient said x-ray locating means including an x-ray tube positionable at two locations for transirradiating a patient from two different directions, and means for generating x-ray images of said patient;

position data generator means for continually generating data identifying the actual spatial position of said means for administering medical therapy preceding and during therapy;

means for generating therapy position data identifying a therapy position for said means for administering therapy at which said means of administering medical therapy administers medical therapy to said patient computer means connected to said position generator means and to said x-ray locating means for automatically controlling positioning of said means for administering medical therapy at said therapy position;

motor driven means controlled by said computer means for positioning said means for administering medical therapy; and said computer means including means for continually comparing the data from said position data generator means with said therapy position data to continually control said means for positioning to adjust the position of said means for administering medical therapy so that said means for administering medical therapy is moved to said therapy position for therapy administration and maintained at said therapy position during medical therapy administration.

2. A medical treatment system as claimed in claim 1 further comprising a monitor for reproducing said x-ray images, and marking means for entering the therapy position on said monitor.

3. A medical therapy system as claimed in claim 1 wherein said means for administering medical therapy is a shock wave generator for in situ disintegration of a calculus.

* * * * *